US005704346A

United States Patent [19]

Inoue

[11] Patent Number: 5,704,346

[45] Date of Patent: Jan. 6, 1998

[54] HIGH FREQUENCY OSCILLATORY VENTILATOR

[76] Inventor: Masaaki Inoue, 5-18, 3-chome, Minami-Rinkan, Yamato-shi, Kanagawa-ken, Japan

[21] Appl. No.: 500,019

[22] Filed: Jul. 10, 1995

[30] Foreign Application Priority Data

Jul. 11, 1994 [JP] Japan .................................... 6-180488

[51] Int. Cl.[6] .................................................... A61M 16/00

[52] U.S. Cl. ................................ 128/204.24; 128/204.18; 128/205.14; 128/205.18

[58] Field of Search ......................... 128/204.24, 204.28, 128/205.14, 205.18, 207.14, 280.22, 205.13, 205.24, 204.21, 205.15, 204.27, 204.25, 204.18

[56] References Cited

U.S. PATENT DOCUMENTS

| | | | |
|---|---|---|---|
| 3,046,979 | 7/1962 | Andreasen | 128/204.08 |
| 3,507,297 | 4/1970 | Dann | 128/205.24 |
| 3,973,564 | 8/1976 | Casden | 128/205.14 |
| 4,067,328 | 1/1978 | Manley | 128/205.14 |
| 4,452,239 | 6/1984 | Maleson | 128/203.15 |
| 4,463,756 | 8/1984 | Thuc | 128/204.21 |
| 4,565,301 | 1/1986 | Hubbard et al. | 128/203.21 |
| 4,592,349 | 6/1986 | Bird | 128/204.25 |
| 4,676,239 | 6/1987 | Humphrey | 128/205.17 |
| 4,788,974 | 12/1988 | Phuc | 128/204.21 |
| 4,941,469 | 7/1990 | Adahan | 128/203.12 |
| 5,509,406 | 4/1996 | Kock et al. | 128/200.24 |

FOREIGN PATENT DOCUMENTS

| | | | |
|---|---|---|---|
| 2063687 | 6/1981 | United Kingdom | 128/204.28 |
| 8604822 | 8/1986 | WIPO | 128/203.12 |

*Primary Examiner*—Vincent Millin
*Assistant Examiner*—V. Srivastava
*Attorney, Agent, or Firm*—Armstrong, Westerman, Hattori, McLeland & Naughton

[57] ABSTRACT

A high frequency artificial breathing device is designed to transmit high frequency pressure vibrations generated by frequent reciprocation of a piston in a vibration producing device to a patient pass, and to vibrate gases in a patient pass. In the present invention, some pressure vibrations generated by the vibration producing device are cut off or absorbed by a cross-sectional area regulating member equipped to a vibration transmitting pass which transmits the pressure vibrations to the patient pass, a changeable volume soft bag, or a bag connected to the vibration producing device through a flow rate regulating member. Cutting off or absorption of some pressure vibrations generated by the vibration producing device varies pressure vibration amplitude transmitted to the patient pass. Therefore, when an exchange amount is adjusted by the artificial breathing device depending on the patient's condition etc., changing a piston stroke is not required during the devise's operation, and a normal rotary motor can be used as a motor for driving the piston.

12 Claims, 7 Drawing Sheets

4 9 8 5 27 10B 28 29 30 35 19 31 33 32 34 36

呼吸用ガス源
モータ
1
2
3
4
5
6
6a
7
8
9
10
11

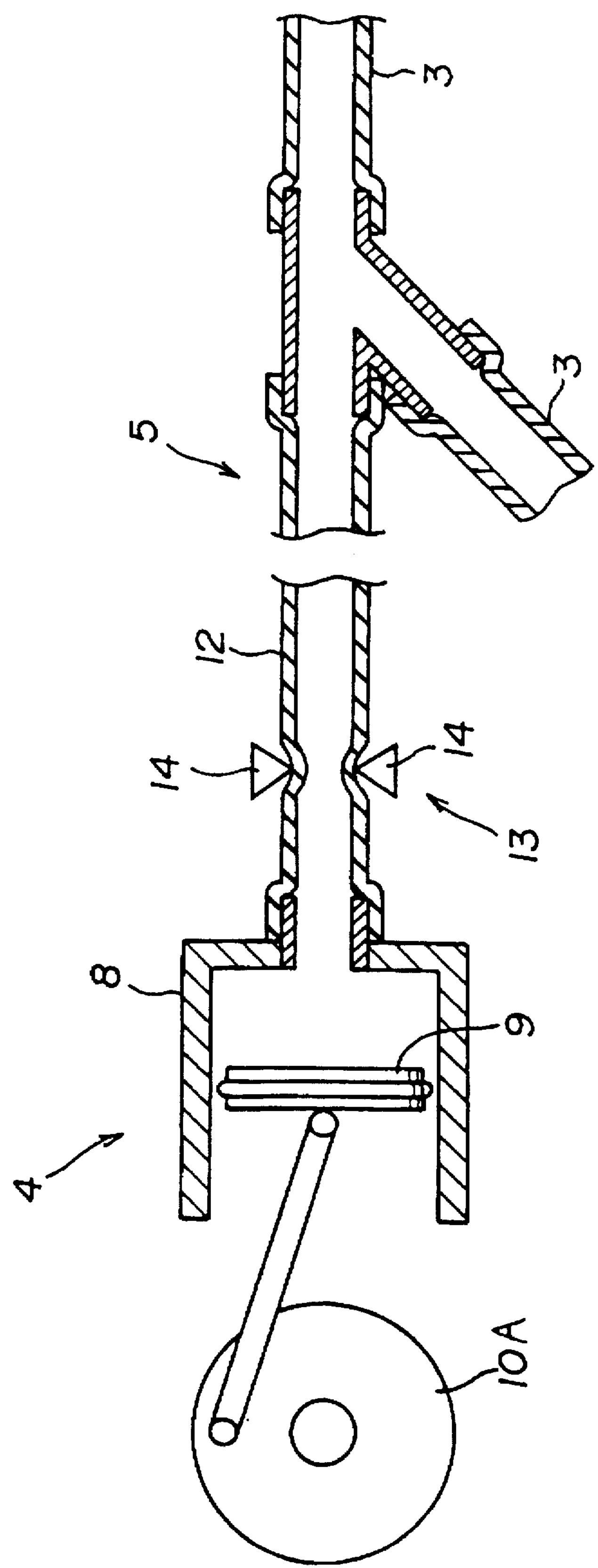
F I G. 2

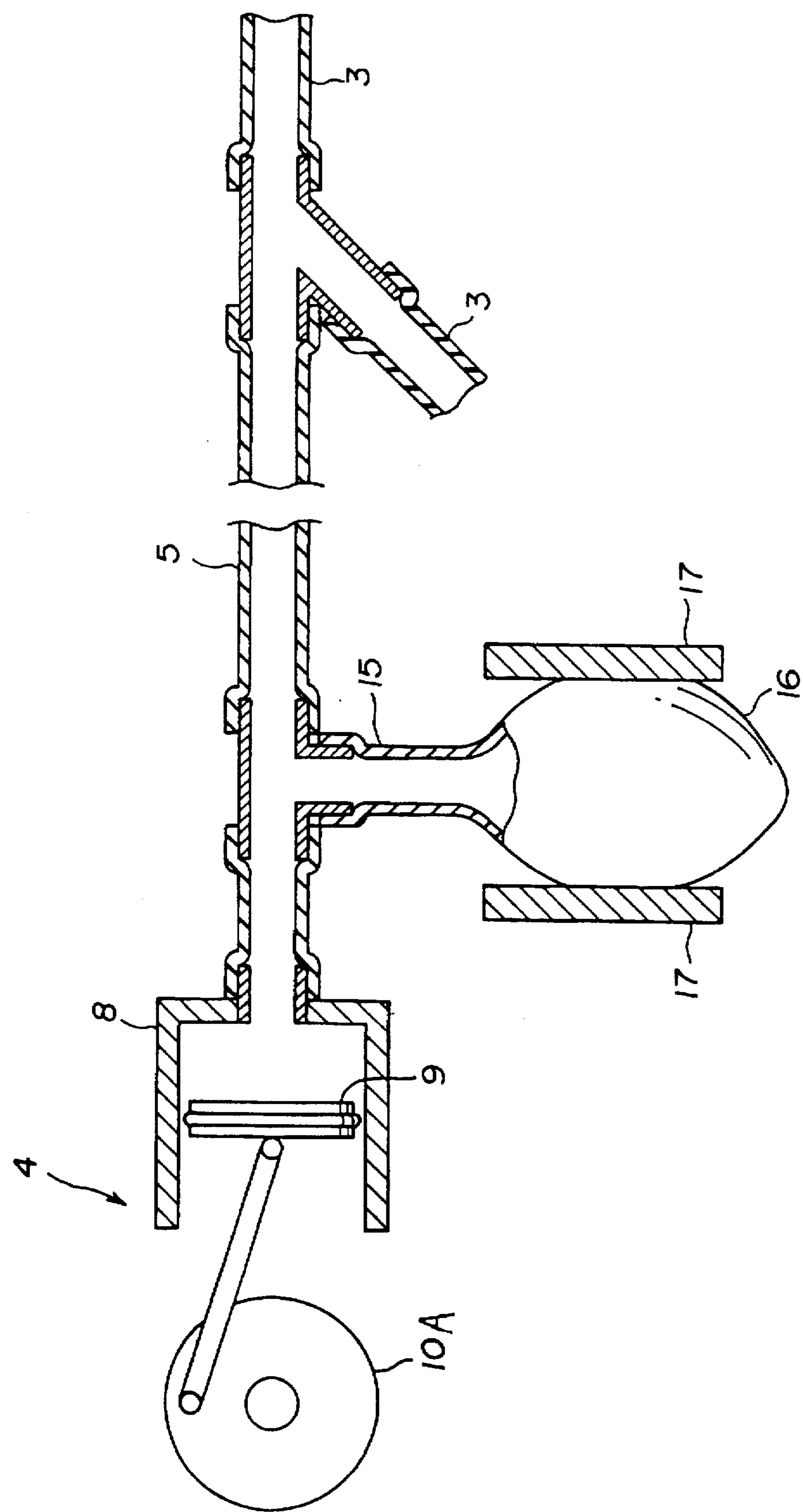
F I G. 3
3
3
5
15
16
17
17
8
9
4
10A

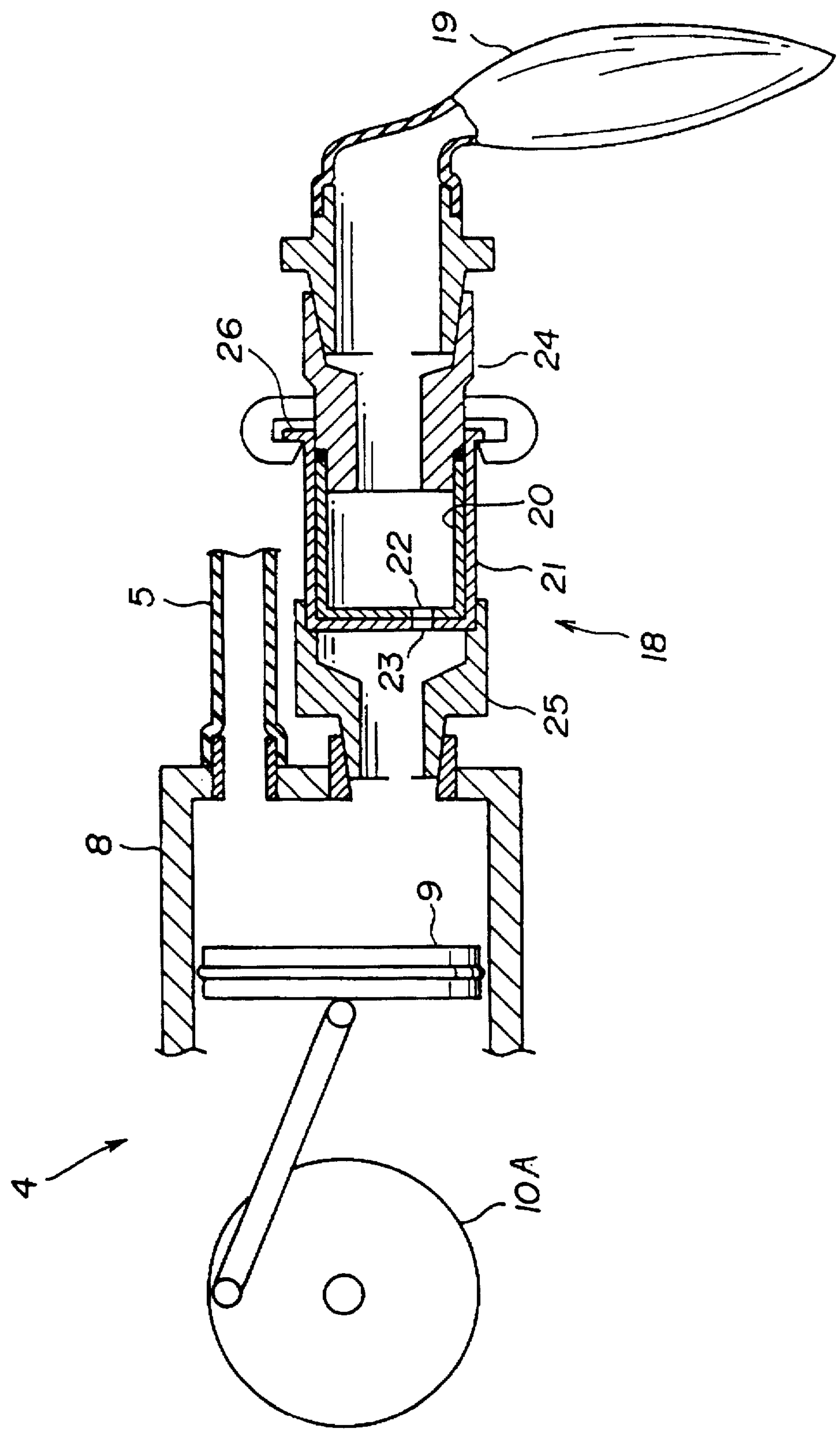
F I G. 4
19
26
24
20
22
21
5
23
18
25
8
9
4
10A

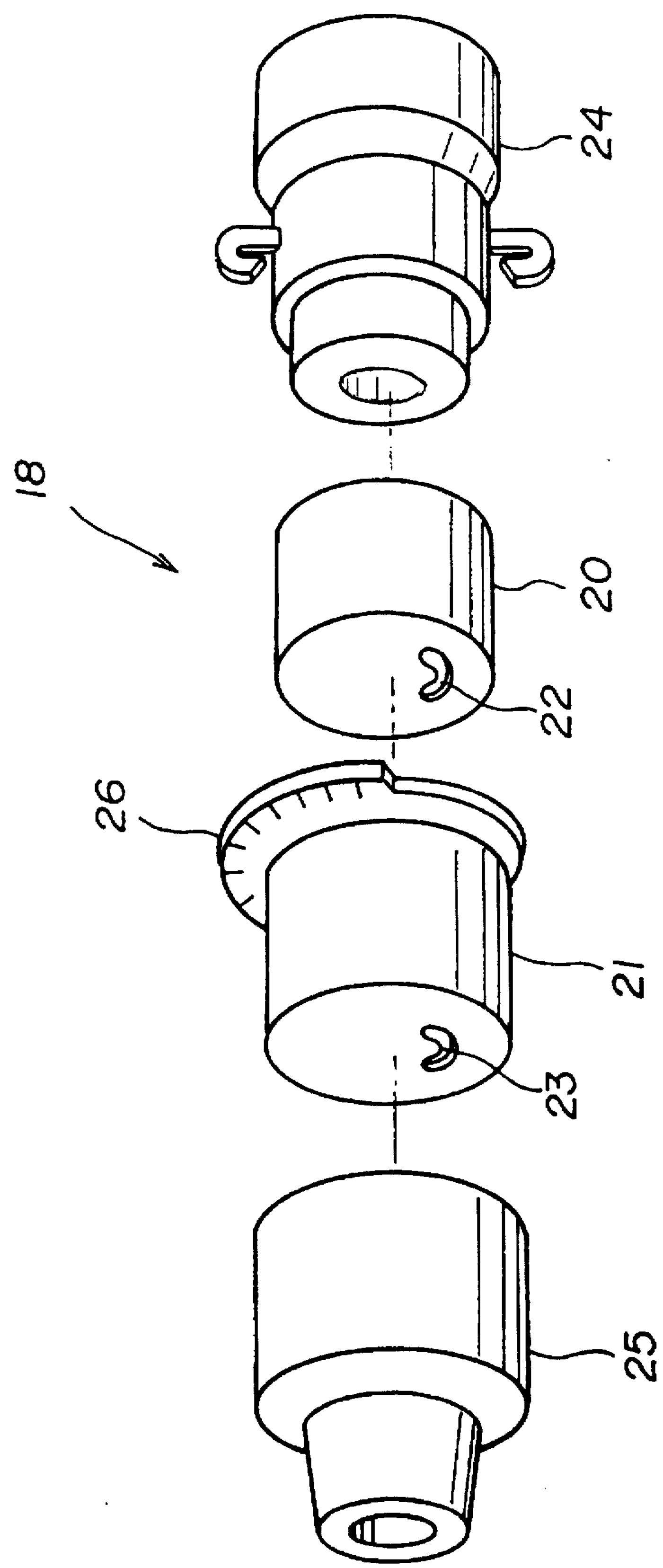
F I G. 5

29
34
33
32
30
31

HIGH FREQUENCY OSCILLATORY VENTILATOR

BACKGROUND OF THE INVENTION

The present invention generally relates to an artificial breathing device which feeds fresh breathing gases to a patient's lungs and substitutes the fresh breathing gases for waste gases, and more particularly, to an artificial breathing device which gives high frequency vibrations to the fresh breathing gases.

The high frequency artificial breathing device of the present invention is designed to carry out artificial breathing in the patient's lungs, without increasing the inner pressure in the patient's trachea, by giving high frequency vibrations to the fresh breathing gases supplied to the patient's trachea from a gas supplying source, in order to enhance gas diffusion in the patient's lungs. A prior art high frequency artificial breathing device, as shown in FIG. 1, generally includes a patient pass 3 and a vibration transmitting pass 5. The patient pass 3 feeds breathing gases, which are supplied by a breathing gas supplying source 1, to the patient's trachea 2 and discharges the surplus breathing gases and the patient's exhaled breath. The vibration transmitting pass 5 transmits high frequency vibration pressure produced by a vibration producing device 4 to the gases in the patient pass 3. The patient pass 3 is equipped with, at an end of the discharging side thereof, a pressure regulator 6 having a nozzle 6*a*, and is exposed to fresh air through the pressure regulator 6. The patient pass 3 is also equipped with, at a middle portion thereof, a trachea positioning tube 7 to be positioned in a patient's trachea. One end of the vibration transmitting pass 5 is connected to an outlet of a cylinder 8 constituting the vibration producing device 4, and the other end thereof is connected to the patient pass 3. A piston 9 is fitted in the cylinder 8, and is designed to be reciprocated by a motor 10 at such high frequencies as about 15 Hz.

In FIG. 1, the numeral 11 denotes a humidifier for moistening the breathing gases.

The above described prior art artificial breathing device is used as follows. Fresh breathing gases are successively supplied to the patient pass 3 from the breathing gas supplying source 1. Back pressure is applied to the patient pass 3 by spraying the breathing gases from the nozzle 6*a* of the pressure regulator 6. Thus, the patient pass 3 and the vibration transmitting pass 5 are always kept pressurized and filled with breathing gas.

With the passes being pressurized, the piston 9 of the vibration producing device 4 is reciprocated at high frequencies. Then, high frequency pressure fluctuations are produced in the cylinder 8 and the pressure waves propagate to the patient pass 3 through the vibration transmitting pass 5. Therefore, the gases in the patient pass 3 vibrate at high frequencies. The vibrations are transmitted to the patient's lungs through the trachea positioning tube 7. As a result, the gases in the patient's lungs vibrate at high frequencies to expedite the gas diffusion, thereby enhancing the exchange of oxygen-carbon dioxide gases occurring in the patient's lungs.

Artificial breathing performed in a patient's lungs by an artificial breathing device requires an adjustment of the gas exchange amount, depending on the patient's condition including, but not limited to, the physical conditioning or physique of the patient. In a high frequency artificial breathing device, an adjustment of the gas vibration pressure amplitude in the patient pass 3 is required.

Conventionally, such an adjustment of the gas vibration pressure amplitude in the patient pass 3 is accomplished by changing the piston stroke of the vibration producing device 4.

However, a normal rotary motor used as a piston driving device may have mechanical difficulties in changing the piston stroke at certain amounts without stopping the motor. Therefore, in a conventional high frequency artificial breathing device, an adjustable stroke linear motor should be used as the motor for driving the piston 9. Such a linear motor is expensive, large and heavy.

Thus, a conventional high frequency artificial breathing device has difficulties in that it has large, bulky parts and is expensive.

SUMMARY OF THE INVENTION

An object of the present invention is to provide an improved high frequency artificial breathing device which can adjust the gas vibration pressure amplitude in the patient pass without changing a piston stroke of the vibration producing device.

Another object of the present invention is to provide an improved high frequency artificial breathing device which is simple in structure and can easily adjust gas vibration pressure amplitude.

In the present invention, these objects are accomplished by intercepting or absorbing some pressure waves which travel from a vibration producing device to a patient pass.

The high frequency artificial breathing device according to the present invention is characterized in that a vibration transmitting pass is equipped with facilities to regulate the cross-sectional area which can vary effective cross-sectional area of the vibration transmitting pass. The facilities to regulate cross-sectional area may include a flexible pipe as a part of the vibration transmitting pass and an adjustable space clamp which deforms the flexible pipe from both sides thereof.

The cross-sectional regulating member installed on the vibration transmitting pass reduces the effective cross-sectional area of the vibration transmitting pass, thereby narrowing the vibration transmitting pass. The narrowed vibration transmitting pass reduces the pressure transmitted to the patient pass through the vibration transmitting pass. The transmitted pressure varies depending on the effective cross-sectional area of the vibration transmitting pass. Therefore, adjusting the effective cross-sectional area of the vibration transmitting pass enables the adjustment of the vibration pressure amplitude transmitted to the patient pass from the vibration producing device.

Further, a high frequency artificial breathing device according to the present invention is characterized in that the device comprises a vibration transmitting pass, a branch pipe branched from the vibration transmitting pass, a soft bag connected to the branch pipe and a expansion restricting member which varies maximum volume of the expanded bag. The expansion restricting member may, for example, be a pair of adjustably spaced rigid plates which clamp the bag from both sides thereof.

The soft bag connected to the vibration transmitting pass expands when the pressure in the vibration transmitting pass becomes high, and contracts when the pressure becomes low. In other words, the pressure fluctuations in the vibration transmitting pass are absorbed by the bag. The absorption amount varies according to the volume of the bag. Therefore, adjusting the maximum volume of the expanded bag enables the adjustment of the pressure vibration amplitude transmitted to the patient pass from the vibration producing device.

Furthermore, a high frequency artificial breathing device according to the present invention is characterized in that the device comprises a cylinder constituting the vibration producing device, soft bag connected to an outlet side of the cylinder, a gas passage connecting the bag and the cylinder and a cross-sectional area regulating member which varies the effective cross-sectional area of the gas passage.

The soft bag connected to the outlet side of the cylinder absorbs some pressure fluctuations produced by the cylinder. The cross-sectional area regulating member, which is equipped with the gas passage connecting the bag and the cylinder for adjusting the effective cross-sectional area of the gas passage, enables the adjustment of the pressure transmitted to the bag, namely absorption pressure. Therefore, the cross-sectional area regulating member can also adjust the pressure vibration amplitude transmitted to the patient pass from the vibration producing device.

Thus, the present invention allows a variance of the pressure vibration amplitude transmitted to the patient pass without providing changeable stroke piston in the vibration producing device. Thus, a rotary motor can be used as a piston driving member, thereby enabling the high frequency artificial breathing device to be reduced in size, weight and cost.

BRIEF EXPLANATION OF THE DRAWINGS

The above-mentioned objects, features and advantages of the present invention will be discussed in the following detailed explanations with reference to the accompanying drawings.

FIG. 2 shows a fragmentary longitudinal sectional view of the first embodiment of the high frequency artificial breathing device according to the present invention.

FIG. 3 shows a fragmentary longitudinal sectional view of the second embodiment of the high frequency artificial breathing device according to the present invention.

FIG. 4 shows a fragmentary longitudinal sectional view of the third embodiment of the high frequency artificial breathing device according to the present invention.

FIG. 5 shows a perspective view of a flow rate regulating valve in a disassembled state, which is used in the high frequency artificial breathing device shown in FIG. 4.

DESCRIPTION OF THE PREFERRED EMBODIMENT

Figure 1:
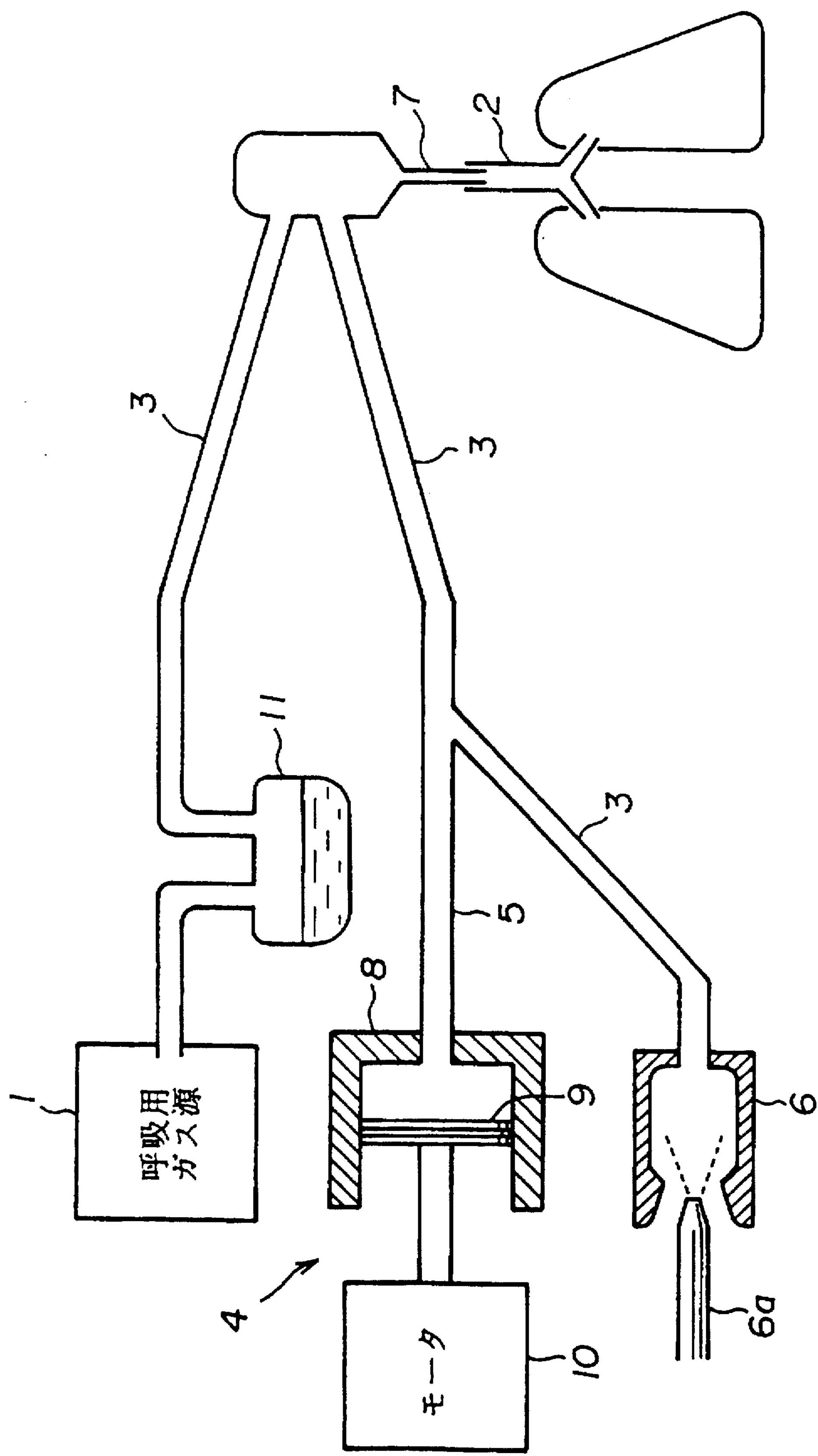
FIG. 1 shows an example of a conventional prior art high frequency artificial breathing device which is to be improved by the present invention.

The improved high frequency artificial breathing device according to the present invention is basically organized the same as the conventional device shown in FIG. 1, such that the numerals in FIG. 1 will be used in the following descriptions.

Referring to in FIG. 2, a vibration transmitting pass 5 is connected to the outlet end of the cylinder 8 constituting the vibration producing device 4 in the high frequency artificial breathing device. The vibration transmitting pass 5 is composed of a flexible tube 12 such as a flexible resin tube, e.g. vinyl chloride resin tube, or rubber tube. The flexible tube 12 is equipped with, on its outer side, a clamper 13 as a cross-sectional area regulating member. The clamper 13 includes a pair of clamping members 14, 14 for pinching the flexible tube 12 from both sides thereof. The distance between the clamping members 14, 14 can be adjusted.

The other end of the vibration transmitting pass 5 is connected to the patient pass 3.

The piston 9 of the vibration producing device 4 is reciprocated at a constant stroke by a rotary motor 10A.

The artificial breathing performed by an artificial breathing device thusly arranged requires the adjustment of the distance between the clamping members 14, 14 depending on the patient's conditioning and/or physique. In the event that a small amount of gas exchange is required, the distance between the clamping members 14, 14 is decreased. Then, the flexible tube 12 is pinched from both sides thereof by the clamping members 14, 14 to be deformed into an oval shape, thereby decreasing the effective cross-sectional area.

In this situation, the motor 10A is operated to reciprocate the piston 9 in the vibration producing device 4 at high frequencies. The reciprocating movement of the piston generates high frequency pressure fluctuations in the cylinder 8, which is transmitted to the vibration transmitting pass 5. In this case, as the vibration transmitting pass 5 is decreased in cross-sectional area by pinching the flexible tube 12 by the clamper 13 as mentioned above, the pressure fluctuations are decreased by the position of the clamper 13. The decreased pressure fluctuations are transmitted to the patient pass 3. Thus, the amplitude of the pressure waves transmitted to the patient pass 3 becomes smaller than that of the pressure fluctuations generated by the vibration producing device 4.

If the vibration transmitting pass 5 is completely closed by the clamper 13, the vibration transmission is completely intercepted. In other words, the pressure vibration amplitude transmitted to the patient pass 3 becomes zero. In contrast, if the vibration transmitting pass 5 is completely opened by releasing the pinching force of the clamper 13, the pressure vibration generated by the vibration generating device 4 is transmitted to the patient pass 3 without decreasing the vibration. In other words, the pressure vibration amplitude transmitted to the patient pass 3 becomes maximum. This means that the pressure vibration amplitude transmitted to the patient pass 3 varies depending on the effective cross-sectional area of the vibration transmitting pass 5 regulated by the clamper 13.

As mentioned above, changing the distance between the clamping members 14, 14 allows the adjustment of the pressure vibration amplitude transmitted to the patient pass 3, so that the stroke of the piston 9 can be kept constant. Therefore, a normal rotary motor 10A can be used as a motor for driving the piston 9.

In the second embodiment shown in FIG. 3, a branch pipe 15 is connected to the vibration transmitting pass 5. The end of the pipe 15 is equipped with a soft bag 16 hermetically connected thereto. The bag 16 is similar to a reservoir bag used in a conventional artificial breathing device, but it must be kept small such as 50 cc in volume.

A pair of rigid plates 17, 17 form an expanding restricting member and are placed at both outer sides of the bag 16. The distance between the rigid plates 17, 17 can be adjusted as desired.

Similar to the first embodiment shown in FIG. 2, artificial breathing performed by a thusly organized second embodiment of the artificial breathing device of the present invention requires an adjustment of the distance between the rigid plates 17, 17 depending on the patient's conditioning and/or physique. In the event that a small amount of gas exchange is required, the distance between the rigid plates 17, 17 must be increased. Then, the motor 10A is operated to reciprocate the piston 9 in the vibration producing device 4 at high frequencies. The advance movement of the piston 9 compresses the gases in the cylinder 8, therefore, the pressure is transmitted not only to the vibration transmitting device 5 but also to the bag 16 through the branch pipe 15 to expand the bag 16. The backward movement of the piston 9 sucks the gases in the bag 16 to shrink the bag 16. This expansion and shrinkage of the bag 16 is performed by some pressure vibrations generated by the vibration generating device 4. Therefore, the bag 16 absorbs some vibration pressure transmitted to the patient pass 3 through the vibration transmitting pass 5 from the generating device 4.

The absorption amount of the vibration pressure depends on the volume of the bag 16. For example, if the volume of a patient's lungs is assumed to be constant, all vibration pressure generated by the vibration generating device 4 is absorbed by the bag 4 when the volume of the bag 16 is equal to the stroke volume of the piston 9. Therefore, pressure vibration amplitude transmitted to the patient pass 3 becomes zero. When the volume of the bag 16 is zero, i.e. the artificial breathing apparatus is not equipped with a bag 16, the pressure vibration generated by the vibration generating device 4 is transmitted to the patient pass 3 without decreasing the vibration. In other words, the pressure vibration amplitude transmitted to the patient pass 3 becomes maximum. This means that the pressure vibration amplitude transmitted to the patient pass 3 varies depending on the volume of the bag 16.

In this embodiment, the maximum volume of the expanded bag is regulated by the rigid plates 17, 17 disposed at both sides of the bag 16. Therefore, the pressure vibration amplitude transmitted to the patient pass 3 can be controlled by adjusting the distance between the plates.

In this way, the same functions and results as in the first embodiment shown in FIG. 2, can be obtained by the artificial breathing apparatus of the second embodiment. A bag 16 such as used in the second embodiment does not apply a heavy load to the motor 10A, even if the pressure vibration amplitude transmitted to the patient pass 3 is minimized. Therefore, problems caused by decreasing the cross-sectional area of the vibration transmitting pass 5 in the first embodiment shown in FIG. 2, such as noise generation and/or overheating of the motor 10A, can be avoided in the second embodiment of the invention.

In the third embodiment shown in FIGS. 4 and 5, a vibration transmitting pass 5 is connected to one end of the cylinder 8 constituting a vibration generating device 4. A soft bag 19, similar to the bag shown in FIG. 3, is connected to the one end of the cylinder 8, an outlet end thereof, through a flow rate regulating valve 18 as a cross-sectional area regulating member. The flow rate regulating valve 18 includes an inner cylindrical pipe 20 and an outer cylindrical pipe 21 both having bottom ends. The inner cylindrical pipe 20 is rotatably and hermetically fitted in the outer cylindrical pipe 21. A circular plate constituting the bottom end of the inner cylindrical pipe 20 has a circular opening 22. Further, a circular plate constituting the bottom end of the outer cylindrical pipe 21 also has a circular opening 23 similar to the opening 22. These openings 22, 23 are arranged on the same radius of the bottom ends of the cylindrical pipes, thereby a rotation of the inner cylindrical pipe 20 relative to the outer cylindrical pipe 21 varies the overlapping area of both the openings.

A pipe joint 24 is connected to the open end of the inner cylindrical pipe 20 and the bag 19 is connected to the joint 24.

The closed end of the outer cylindrical pipe 21 is connected to another pipe joint 25 and the pipe joint 25 is connected to the cylinder 8. The inner cylindrical pipe 20 can be rotated with the bag 19 relative to the outer cylindrical pipe 21 fixed to the cylinder 8. A flange 26 is equipped to an open end of the outer cylindrical pipe 21. The flange 26 has a scale mark showing relative rotational angle between the inner cylindrical pipe 20 and the outer cylindrical pipe 21.

In this third embodiment of a high frequency artificial breathing device, some pressure vibration generated by the vibration generating device 4 is absorbed by the bag 19.

An adjustment of the overlapping area of the openings 22 and 23 of the inner and outer cylindrical pipes 20 and 21, respectively, by rotating the inner cylindrical pipe 20 of the flow rate regulating valve 18 relative to the outer cylindrical pipe 21, can vary the absorption amount of the vibration pressure for the reasons as follow. The cylinder 8 and the bag 19 are connected in fluid communication with each other through the overlapping area of the openings 22 and 23 of the inner and outer cylindrical pipes 20 and 21. When the overlapping area is reduced, the gas flow rate between the cylinder 8 and the bag 19 decreases. Thus, the absorption pressure amount of the bag 19 decreases, thereby increasing pressure wave amplitude transmitted to the patient pass 3 from the vibration transmitting pass 5. On the other hand, when the overlapping area of the openings 22 and 23 is increased, the gas flow rate between the cylinder 8 and the bag 19 increases. Thus, the vibration pressure amplitude transmitted to the patient pass 3 becomes small.

As mentioned above, the vibration pressure amplitude transmitted to the patient pass 3 can be adjusted by regulating the effective cross-sectional area of the gas passage which connects the cylinder 8 and the bag 19.

Thus, the third embodiment of the invention can obtain results and effects similar to the first and second embodiments. Further, in the third embodiment, the flow rate regulating valve 18 and the bag 19 are directly connected to the cylinder e of the vibration generating device 4. Therefore, the valve 18 and the bag 19 are easily supported by the cylinder 8 so that the flow rate regulating valve 18 can be operated easily and certainly.

Figure 6:
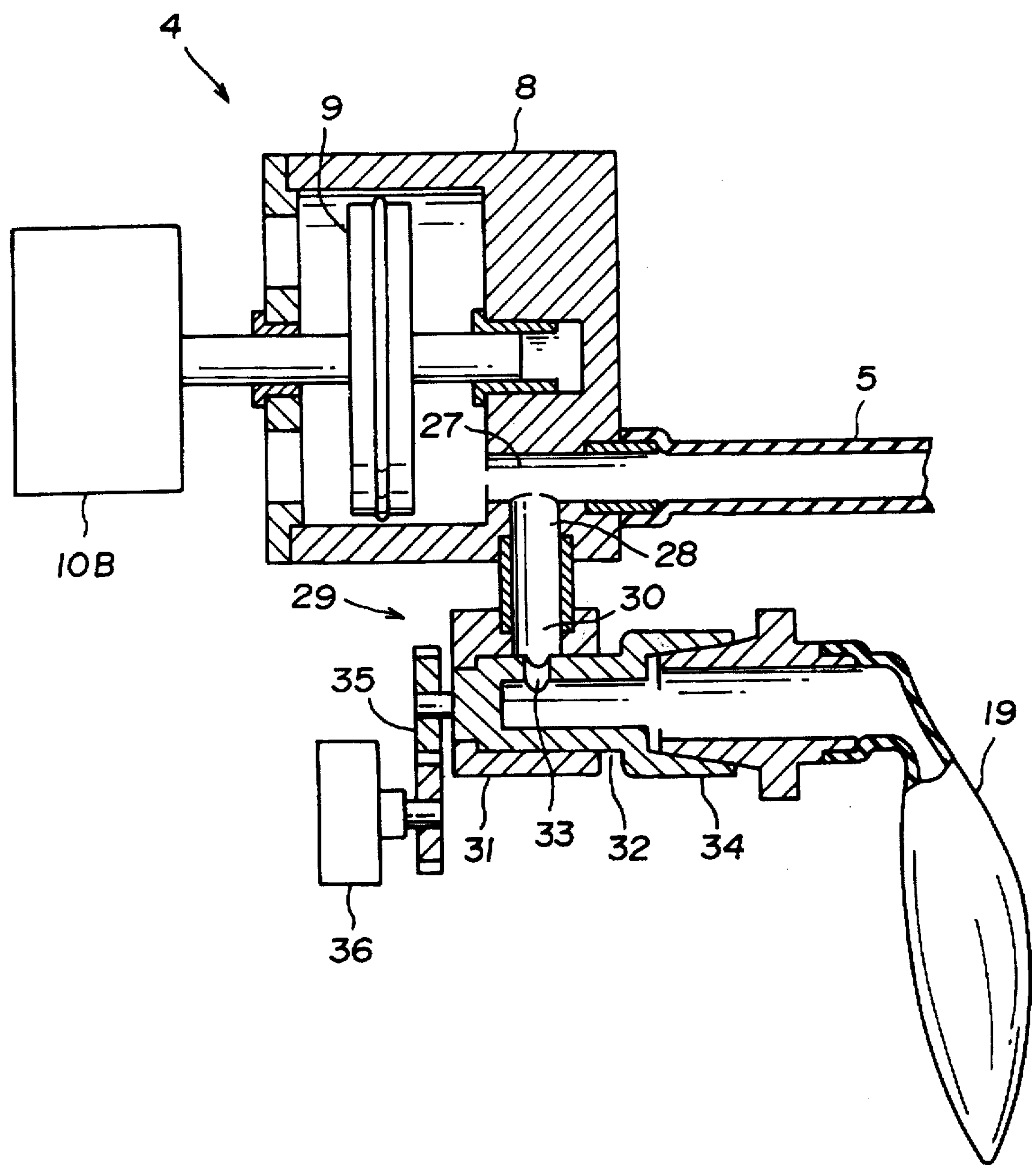
FIG. 6 shows a fragmentary longitudinal sectional view of the modified embodiment of the high frequency artificial breathing device shown in FIG. 4.
Figure 7:
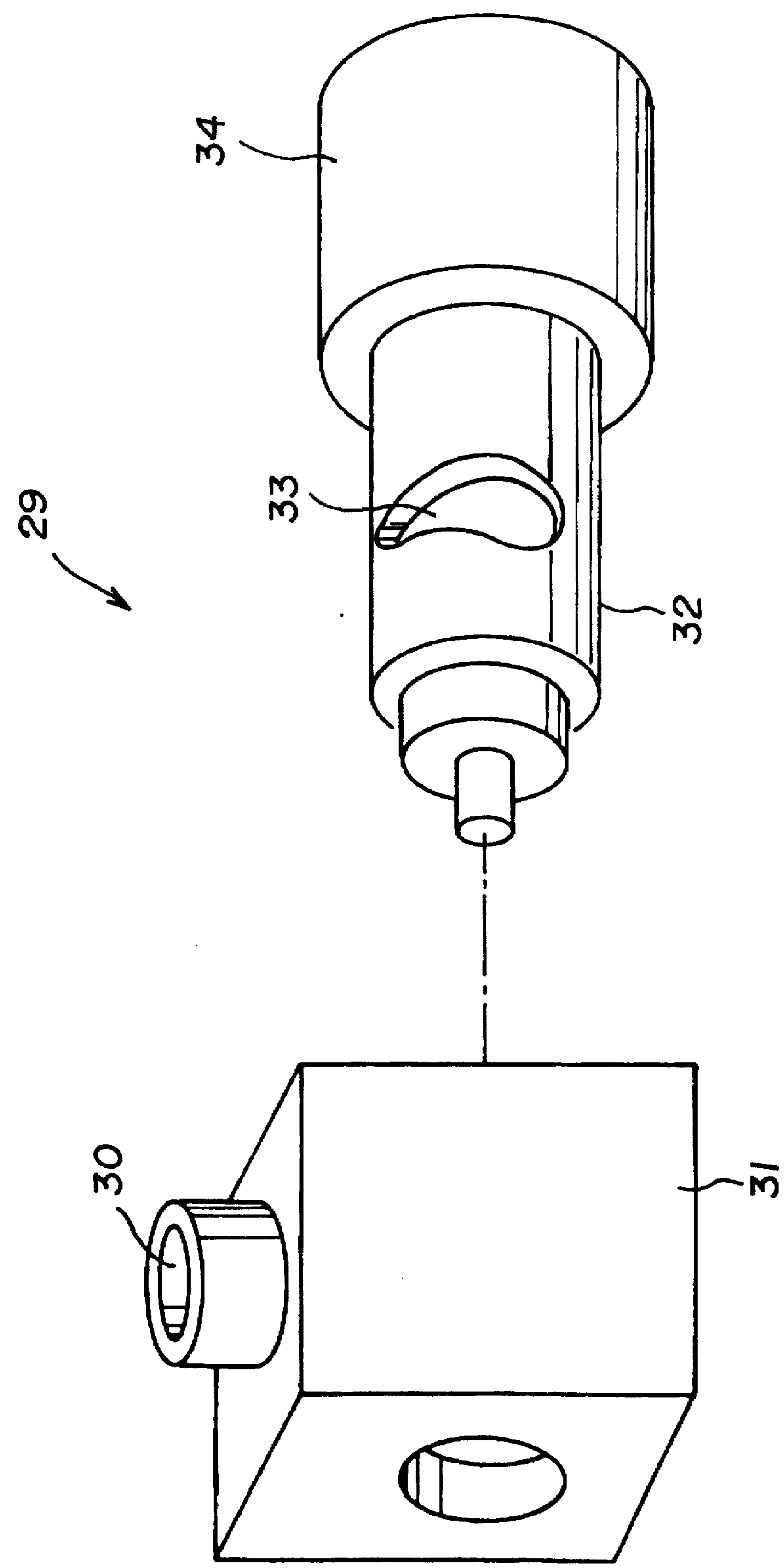
FIG. 7 shows a perspective view of a flow rate regulating valve in a disassembled state, which is used in the high frequency artificial breathing device shown in FIG. 6.

FIG. 6 and FIG. 7 show a fourth embodiment of the artificial breathing apparatus according to the present invention. The forth embodiment is a modification of the third embodiment shown in FIG. 4 and FIG. 5.

As is apparent from FIG. 6, in the fourth embodiment, a linear motor 10B, which is similar to a linear motor used in a conventional high frequency artificial breathing device, is used as a motor for driving the piston 9 in the vibration producing device 4. However, the motor 10B is not equipped with driving stroke regulating members and keeps constant stroke of the piston 9. The outlet end wall of the cylinder 8 constituting the vibration producing device 4 is thick-walled, and a patient gas passage 27 connected to the vibration transmitting pass 5 and a branch gas passage 28 branched from the patient gas passage 27 are formed in the end wall. A bag 19 communicates with the branch gas passage 28 through a flow rate regulating valve 29 as a cross-sectional area regulating member. The flow rate regulating valve 29 includes a valve body 31 having a cylindrical port 30 connected to the branch gas passage 28 and an inner cylindrical pipe 32 having a bottom end which is rotatably and hermetically fitted in the valve body 31.

As shown in FIG. 7, the peripheral wall of the inner cylindrical pipe 32 has an opening 33 which extends in a circumferential direction and gradually decreases the width from one longitudinal end of the opening toward the other longitudinal end thereof. The opening 33 is positioned to face the port 30 of the valve body 31. Thus, an opening area of the port 30 facing the opening 33 varies by rotating the inner cylindrical pipe 32 around the axis.

A bag 19 is connected to the opening end of the inner cylindrical pipe The opening end of the inner cylindrical pipe 32 juts out from the valve body 31 and constitutes a rotational knob 34. The closed end of the inner cylindrical pipe 32 is equipped with a gear mechanism 35 which transmits the rotation of the inner cylindrical pipe 32 to a rotational angle sensor 36. Thus, the rotational angle of the inner cylindrical pipe 32 is detected by the sensor 36 and shown on a display (not shown).

In the high frequency artificial breathing device, the pressure waves generated by the cylinder 8 are introduced into the bag 19 through overlapping portions of the port 30 of the valve body 31 and the opening 33 of the inner cylindrical pipe 32. The overlapping area varies by rotating the inner cylindrical pipe 32 around the axis. Therefore, like the third embodiment shown in FIG. 4 and FIG. 5, the fourth embodiment has an effective cross-sectional area of the gas passage connecting the cylinder 8 and the bag 19 which becomes adjustable, thereby enabling the control of the vibration pressure amount absorbed by the bag 19. As mentioned above, the fourth embodiment can also adjust the pressure vibration amplitude transmitted to the patient pass 3 without changing stroke of the piston 9 in the vibration producing device 4.

In the above mentioned first embodiment, a clamper 13 is used for a cross-sectional area regulating member of the vibration transmitting pass 5. However, the flow rate regulating valve 18, 29 shown in the third or fourth embodiment, or similar, may also be used for the cross-sectional area regulating member. In this case, a pipe joint connecting the flow rate regulating valve and the vibration transmitting pass 5, must allow relative rotation therebetween.

The artificial breathing device requires once used parts in the passes to be sterilized or to be disposed of. Therefore, the parts should be simple in construction to be low in cost. Use of a rotational pipe joint causes complicated structure and increases cost. A clamper does not require sterilization because it is installed outside of the passes.

Therefore, in the third or fourth embodiment, the gas passage connecting the cylinder 8 and the bag 19 may be a flexible tube and a clamper, as shown in the first embodiment, may be used as a cross-sectional area regulating member of the gas passage. However, the accurate adjustment of the cross-sectional area is not achieved by deforming the flexible tube by the clamper. In the third or fourth embodiment, as the bag 19 can be rotated with the inner cylindrical pipe 20, 32 of the flow rate regulating valve, a rotational pipe joint is not required to be interposed therebetween. Therefore, the flow rate regulating valve 18, 29 can be provided at a low cost.

Further, each of the technical members mentioned in the first, second, third and fourth embodiment is not limited to individual use, but can be used in combination.

What is claimed is:

1. A high frequency artificial breathing device comprising:

a patient pass having two ends with a first end connected to a breathing gas supplying source, a second end exposed to open air through a pressure regulator and a middle portion connected to a trachea positioning tube;

a cylinder having a piston and a motor for reciprocating said piston frequently;

a vibration transmitting pass having two ends with a first end connected to said patient pass and a second end connected to said cylinder equipped with said piston which is reciprocated frequently by said motor, wherein high frequency vibration pressure generated by reciprocal movement of said piston is transmitted to gases in said patient pass;

means for absorbing some pressures generated by reciprocal movement of said piston in said cylinder, wherein said absorbing means is a soft bag connected to an outlet of said cylinder; and a cross-sectional area regulating means for varying effective cross-sectional area of a gas passage which connects said bag to said cylinder.

2. The high frequency artificial breathing device as recited in claim 1, wherein said cross-sectional area regulating means comprises circular plate means for allowing relative rotational movements with overlapping areas, each of said plate means having an opening wherein said overlapping area of both said openings can be varied by relative movement of said circular plate means.

3. The high frequency artificial breathing device as recited in claim 1, wherein said cross-sectional area regulating means comprises a valve body and a cylindrical inner pipe rotatably fitted in said valve body, said inner pipe having a peripheral wall with an opening, said cross-sectional area varying in a circumferential direction of said valve body having a port facing said opening.

4. The high frequency artificial breathing device of claim 1, wherein said motor is a linear motor which keeps a constant stroke of said piston, but which is not equipped with driving stroke regulating members that add to the size, weight and expense of said device.

5. The high frequency artificial breathing device of claim 1, wherein said cylinder has an outlet end wall that is of a greater thickness than a cylindrical wall of said cylinder.

6. The high frequency artificial breathing device of claim 5, wherein said outlet end wall of said cylinder has said patient pass through said thickness thereof.

7. The high frequency artificial breathing device of claim 6, wherein a branch gas passage is connected to said patient pass in a direction transverse to said thickness of said outlet end wall of said cylinder.

8. The high frequency artificial breathing device of claim 7, wherein said branch gas passage is connected to a cylindrical port of a flow rate regulating valve.

9. The high frequency artificial breathing device of claim 8, wherein said cylindrical port of said flow rate regulating valve is attached to a valve body and is adjacent to an opening in an inner cylindrical pipe which is housed in said valve body and said inner cylindrical pipe is attached to a rotational knob.

10. The high frequency artificial breathing device of claim 9, wherein said opening in said inner cylindrical pipe leads to a chamber within said inner cylindrical pipe which leads to a chamber within said rotational knob which in turn is connected to said soft bag.

11. The high frequency artificial breathing device of claim 10, wherein said inner cylindrical pipe has a closed end which is equipped with a gear means for transmitting rotation of said inner cylindrical pipe to a rotational angle sensor means.

12. The high frequency artificial breathing device of claim 11, wherein rotational angle sensor means detects and displays a rotational angle of said inner cylindrical pipe.

* * * * *